United States Patent [19]

Kenney

[11] Patent Number: 4,636,339
[45] Date of Patent: Jan. 13, 1987

[54] METHOD FOR IN-PROCESS MULTI-ELEMENT ANALYSIS OF MOLTEN METAL AND OTHER LIQUID MATERIALS

[75] Inventor: George B. Kenney, Medfield, Mass.

[73] Assignee: Metallurgical Instruments, Inc., Lexington, Mass.

[21] Appl. No.: 768,493

[22] Filed: Aug. 22, 1985

Related U.S. Application Data

[62] Division of Ser. No. 522,913, Aug. 12, 1983, Pat. No. 4,578,022.

[51] Int. Cl.$^4$ .............................................. B22F 9/08
[52] U.S. Cl. ...................................... 264/12; 264/40.1; 356/316
[58] Field of Search ................ 264/5, 12, 13, 15, 40.1, 264/169; 425/6, 7; 356/313, 316

[56] References Cited

U.S. PATENT DOCUMENTS

| | | | |
|---|---|---|---|
| 1,501,449 | 7/1924 | Hall | 425/7 |
| 2,638,626 | 5/1953 | Golwynne | 425/7 |
| 3,293,334 | 12/1966 | Bylund et al. | 425/7 |
| 3,606,540 | 9/1971 | Williams et al. | 356/313 |
| 4,468,182 | 8/1984 | Booz et al. | 425/7 |

Primary Examiner—Jay H. Woo
Assistant Examiner—J. Fortenberry
Attorney, Agent, or Firm—Bromberg, Sunstein & McGregor

[57] ABSTRACT

A method for generating an aerosol powder from a melt includes an atomization die having an orifice through which the melt passes to create the powder. In a preferred embodiment, the orifice has a dimension less than 5 millimeters, and may include a heater to prevent freeze-off. The die may be included in a high-temperature probe suitable for immersion on the melt, so that accumulated accretions of powder on the walls of the probe may be melted off by heating the probe.

4 Claims, 4 Drawing Figures

METHOD FOR IN-PROCESS MULTI-ELEMENT ANALYSIS OF MOLTEN METAL AND OTHER LIQUID MATERIALS

This is a divisional of co-pending application Ser. No. 522,913 filed on Aug. 12, 1983, now U.S. Pat. No. 4,578,022.

DESCRIPTION

1. Technical Field

The present invention relates to methods and equipment for providing rapid in-process, multi-element analysis of molten metals, alloys, metallurgical baths, and other liquid materials.

2. Background Art

The chemical balance or elemental composition of a material directly determines the characteristics of that material's microstructure and subsequent properties and performance. The final elemental composition of a metal is generally determined by alloying and/or the primary process by which the material is produced. Therefore, it is imperative that the final elemental composition of materials, such as steel, be controlled accurately to ensure the consistency of its physical, mechanical, electrical, and magnetic properties and performance in service. The ability to monitor the in-process elemental composition of a liquid phase primary metal process, such as steelmaking, and subsequent alloying operations, would guarantee the chemistry, subsequent properties, and performance of the product.

In current metallurgical practice, the elemental analysis of the molten metal or alloy is accomplished by physically extracting from the melt a liquid sample which is quickly solidified and analyzed by either chemical or spectrometric means. If the appropriate chemistry is found to exist, the metallurgical process is terminated and the metal is poured. If the desired chemistry has not yet been obtained, the smelting or refining process is continued and the chemical analysis procedure is repeated. For example, for many basic oxygen steelmaking heats, the elemental analysis of one turndown sample is adequate to confirm that the steel has been made to specifications. However, when the chemistry is off and a reblow is required, another turndown sample must be taken and analyzed. Typically, an average of 1.5 samples are taken per heat, which represents up to 20 percent of the average 60 minute-cycle time required to refine a heat of steel. The delay or dead-time inherent to steelmaking as well as other metallurgical processes due to current elemental analysis procedures not only retards the productivity and efficiency of the process, but may also provide misleading results because the chemical activity of the process continues during the holding period required to conduct the analysis. A rapid in-process elemental analysis procedure would vastly improve the productivity, energy efficiency, quality, and economics of many metallurgical and other liquid phase processes and products.

Most past efforts to provide rapid, in-process, elemental analysis of molten metal systems were based on the use of an emission spectrometer, with spectral excitation data taken directly from a molten metal surface, or a plasma/ultraviolet spectrometer, analyzing powder produced from the molten metal. Efforts to perform spectrometric analysis directly from the surface of molten systems are described in U.S. Pat. Nos. 3,645,628; 3,659,944; 3,669,546; and 3,672,774. The inherent constraint to the practical application of this approach is the problem of proximity; that is, the stability and functionality of spectrometer equipment cannot be maintained in the immediate vicinity of an operating basic oxygen steelmaking furnace and many other metallurgical processes.

British efforts to provide spectral analysis based on metal powders generated from molten steel are outlined in U.S. Pat. No. 3,606,540. The problems with this technique include interruption of particle flow due to clogging of the lance and difficulty in positioning the jet tube. The lance clogging problem limits this probe method to a single analysis of three minutes or less duration. Once clogged, this lance must be replaced, which renders it neither cost nor time efficient. A variation on this technique (U.S. Pat. No. 3,602,595) generates metal powder by applying an arc to the surface of the molten metal. Spectral analysis of these arc-generated metal powders has also been found to be unreliable. While considerable laboratory work has been done on these and other techniques in the United Kingdom and in France during the 1960's and early 1970's, no technique has been reduced to routine practice in an industrial environment.

DISCLOSURE OF INVENTION

The present invention provides a probe apparatus for generating an aerosol powder from a melt. In a preferred embodiment, the invention includes an atomization die having an orifice through which the melt passes to create an aerosol powder; the orifice in this embodiment is in the size range at and immediately above that which is just sufficient to permit continuous generation of such powder by flow of the melt therethrough and in-process analysis of such powder. The die may be included in a high-temperature probe suitable for immersion in the melt, so that accumulated accretions of powder on the walls of the probe may be melted off by heating the probe.

BRIEF DESCRIPTION OF DRAWINGS

These and other objects and features of the invention will be more readily understood by consideration of the following detailed description taken with the accompanying drawings, in which.

DESCRIPTION OF SPECIFIC EMBODIMENTS

The preferred embodiments of the invention are described in the context of analyzing molten metals and alloys, specifically ferrous systems. However, the invention is equally applicable to the analysis of any liquid from which a fine aerosol can be generated. For example, this includes but is not restricted to molten metals, alloys, slags, electrolytic baths, and other melts or processing solutions. (The term "melt" as used in this description and the following claims will be understood to include any liquid suitable for processing in accordance with the present invention.)

Figure 1:
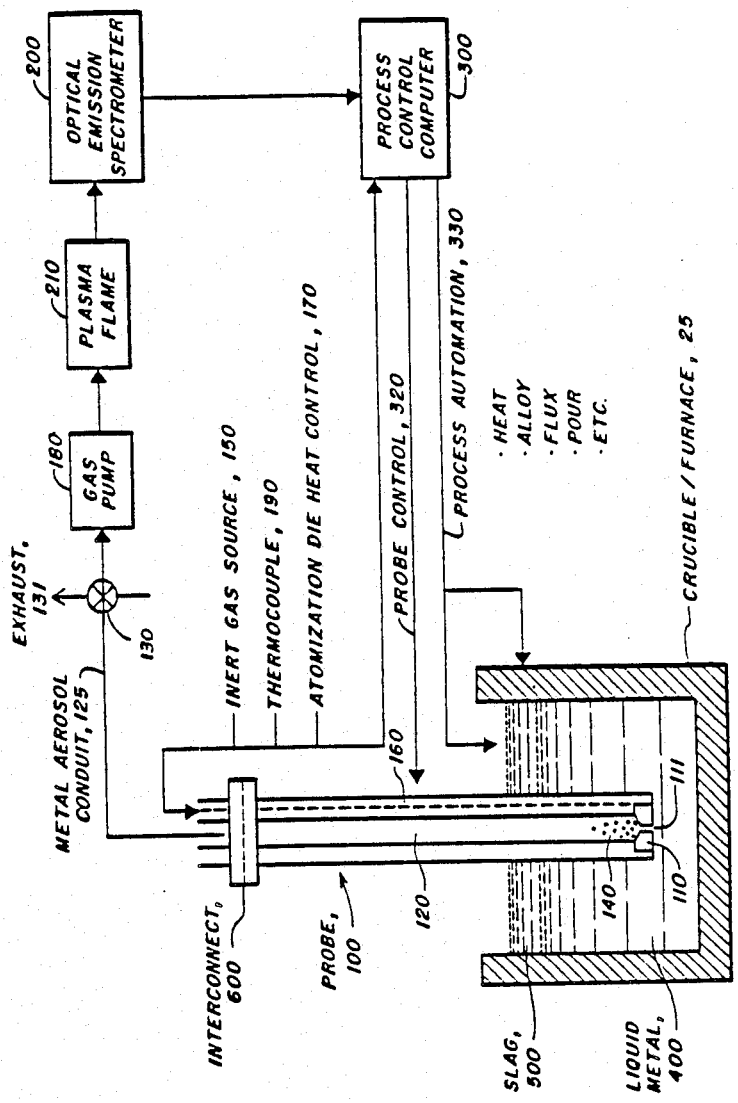
FIG. 1 is a schematic overview of the liquid metal atomization probe used to produce the fine metal aerosol powders which are fed to a plasma flame for analysis using an emission spectrometer. The results of this spectral elemental analysis represent the data necessary to provide automatic or manual feedback control to the process being analyzed.

Referring now to FIG. 1, a perspective view is shown of the rapid in-process elemental analyzer system, consisting of the metal atomization probe sampling device 100 and an elemental analysis system, the latter including plasma flame 210, optical emission spectrometer 200 and process feedback control 300. The probe has a gas operated metal atomization die 110, a metal aerosol conduit/delivery system 120, and a probe/aerosol conduit interconnection 600. Throughout the description of the device, item numbers are uniform so that the numbers used in one figure to identify a feature of the device will identify the same feature of the device in any subsequent figure. Furthermore, it will be appreciated by one versed in the art that the invention is intended for use in a thermal environment in which large and abrupt temperature changes will occur, so that protection against thermal shock may require the use of generally rounded or tapered contours of the device in certain areas. Accordingly, while the drawings, for purposes of illustration, show generally the use of right cylindrical components, angular vertices, and squared-off counterbores, it is understood that the device will generally be formed with contours configured to minimize the complications of thermal shock in a manner well known in the art.

Returning now to FIG. 1, the metal aerosol sample 140 is produced by passing pressurized inert gas 150, such as argon or nitrogen, through the atomization die 110. The inert gas 150 is delivered to the atomization die 110 via the gas delivery passage 160 along the probe body 100. This high pressure gas 150 exits the atomization die 110 at high velocity, thereby aspirating liquid metal 400 up into the probe 100 via the atomization die orifice 111. Upon exiting the die 110, the molten metal 400 is atomized and rapidly solidified by the impinging, high-velocity gas jet. The metal aerosol 140 thus created is subsequently carried along the probe core conduit 120 to the aerosol delivery system 125 by the flow of inert gas 150. (The term "aerosol" as used in this description and the following claims will be understood to include a dispersion of fine particles in any suitable gas or gas mixture.)

The aerosol sample is transported by the inert gas 150 with the assistance of the gas pump 180 and is delivered to an inductively coupled plasma torch 210. The plasma heats and excites the metal powders, causing these particles to emit atomic spectra characteristic of their constituent elements. The specific frequencies of the emitted spectra identify the constituent elements while the intensities of the radiation indicate the quantities of each element present. Since the metal aerosol 140 consists entirely of atomized liquid metal 400 taken directly from the bath, the elemental composition of the aerosol powder 140 corresponds precisely to that of the liquid metal bath 400.

The spectral elemental analysis of the aerosol powder 140 can be accomplished with a standard emission spectrometer 200 aligned to view the emission of the plasma torch 210. A standard emission spectrometer usually has a built-in computer which performs and presents the data analysis. The computer can be expanded or supplemented to provide a process feedback control system 300. With the elemental analysis results in hand, the process control computer 300 compares these with the desired elemental specifications and then, either directly or through an operator, calls for specific action to be taken. This might include, in the case of basic oxygen furnace (BOF) steelmaking, discontinuing the blow, removing the probe, and pouring the heat if the analysis satisfies the specifications, or continuing the heating, alloying, fluxing, and elemental analysis procedures if the analysis and specifications do not match.

Figure 2:
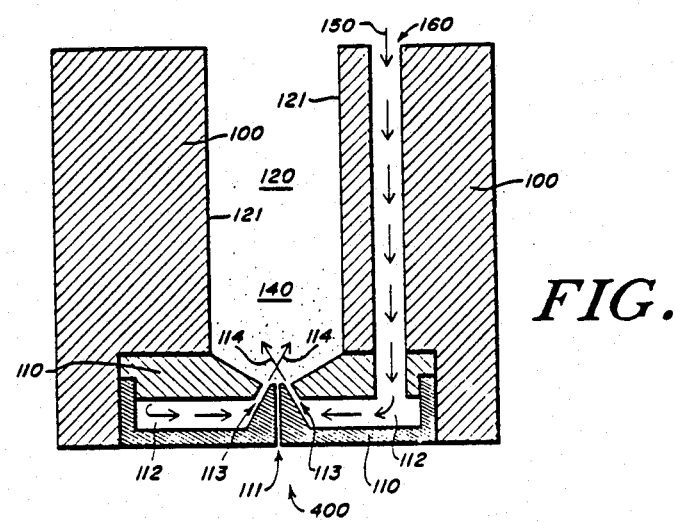
FIG. 2 is a detailed view of a preferred embodiment of the invention showing the main probe body, gas atomization die, and gas delivery system.

FIG. 2 illustrates the gas atomization section of the probe 100. While the probe 100 is always illustrated in a vertical position with the atomization die 110 at the bottom, the probe in this embodiment is functional in any position above the horizontal, as long as its tip is submerged in a molten bath. (Other embodiments of the invention may be used in an inverted orientation.) Furthermore, the probe can be used at any bath depth or position.

The rapid, in-process, elemental analysis probe is based on the principle of generating a fine metal powder aerosol 140 suitable for continuous analysis in an inductively coupled plasma-based emission spectrometer. The metal aerosol 140 is generated using a two-piece gas atomization die 110. High pressure inert gas 150 is supplied to the atomization die 110 via a conduit 160 which is preferably within the probe body 100. The inert gas 150 fills the annular core 112 of the atomization die 110 and passes at high velocity into the core of the probe 120 via an inclined annular nozzle 113 which circumscribes the top of the atomization die orifice 111. The passage of the high velocity inert gas 150 over the top of the atomization die orifice 111 reduces the pressure within the orifice passage 111, assisting liquid metal 400 to rise through the orifice 111. The liquid metal 400 is aspirated through the orifice 111 with the assistance of the head pressure of the liquid metal bath. As the aspirated liquid metal exits the orifice 111 and enters the probe core 120, it is atomized by the impinging inert gas jet 114 exiting the atomizer nozzle 113. The inclination angle of the impinging gas jet can be modified from one liquid metal to another to optimize the aspiration lift effect on the liquid metal and the subsequent atomization of the liquid metal jet. The atomized liquid metal 140 is rapidly solidified by this high velocity, expanding inert gas jet 114. The inert gas flow along the body of the probe 120 lifts and carries the finely atomized metal powder, creating the metal aerosol 140 which flows to the inductively coupled plasma 210 for elemental analysis.

A critical problem with past efforts using atomized metal powders in continuous elemental analysis procedures of liquid metals has been metal buildup on the inside of the probe wall 121, which can completely clog the probe core 120 in a matter of minutes. Once clogged, these earlier probes had to be discarded after as few as one analysis procedure. To compensate for metal buildup on the internal probe walls of previous designs, extraordinary supplementary gas flow procedures and other measures were taken by others with minimal success.

The current invention offers a solution to the clogging problem and is designed to be used for multiple consecutive analysis procedures. The current probe 100 is constructed substantially of ceramics, which eliminate the need for protective gas or liquid cooling of the probe body 100 or atomization die 110. This does not eliminate metal buildup on the inside walls of the probe 121 per se. However, metal buildup can be eliminated during or between analysis procedures. At the completion of a particular analysis procedure, the four-way metal aerosol conduit valve 130 is closed (FIG. 1) and positive inert gas pressure is maintained within the probe 120 via the inert gas conduit 160. With near zero gas flow through the probe 100, it rapidly rises to the temperature of the molten bath within which it is submerged. Consequently, the metal buildup on the probe walls 121 melts and collects in the bottom of the probe 120. The positive inert gas pressure within the probe 120 forces the liquid metal to exit the probe 120 via the die orifice 111. For example, in BOF steelmaking, this procedure could be performed prior to any analysis procedure, to melt off the accretions accumulated inside the probe during the previous sample. Specifically, the elemental analysis of the steel heat is required only towards the completion of the 60-minute processing cycle. This allows more than ample time to purge the probe of any metal residue which might remain from the previous melt by using the heating capacity of the current melt. This procedure is impossible with previously contemplated cooled probes because the internal metallic construction severely limited the allowable internal temperatures.

Previous efforts to use gas atomization probes in conjunction with spectral elemental analysis have also failed or been seriously constrained by metal freeze-off within the gas atomization die. Past efforts to avoid metal freeze-off within the atomization die have focused on increasing the internal diameter of the orifice (on the order of 6 mm to 13 mm) resulting in an increase in the volume of metal flow. This increased volume of metal flow delivers additional heat to the atomization die which is simultaneously being cooled by the atomization gas jet. Such metal flow, which is far greater than would be necessary simply to generate samples for plasma spectroscopy, in effect heats the die and keeps the orifice from freezing off. In practice, the internal diameter of the die orifice is probably somewhat reduced due to the formation of a solidified metal sleeve within the orifice during the atomization process. Controlling the thickness of this metal sleeve and, therefore, the operational orifice diameter has proven difficult. The larger orifice diameter also requires higher gas flow rates, and the subsequent higher metal powder production rates aggravate the metal buildup problem within the probe. The functional life cycle of previous experimental probes has been limited to less than three minutes before the probe core becomes clogged, requiring that it be replaced or discarded.

Prior probe designs, as noted, required a large atomization die orifice 111. However, with the present invention, it has been found that a smaller orifice 111 not only facilitates the production of a more uniform and very fine metal powder 140 but also retards the rate of metal buildup on the interior wall of the probe 121 because of the lower metal powder production rate. With the current invention, the diameter of the die orifice 111 is kept to a minimum, sufficient only to supply the continuous volume of metal aerosol necessary to facilitate emission spectroscopy. The lower limit of the orifice diameter 111 is the minimum diameter through which the liquid metal to be analyzed will flow in response to the head pressure of the melt bath and the aspiration force of the atomization gas jet, working against the surface tension of the liquid metal. Minimizing the flow of liquid metal to that necessary for elemental analysis serves to reduce the rate of metal buildup on the interior wall of the probe 121 and, therefore, maximizes the period of time over which the probe may be operated continuously or intermittently without purging or replacement. The cycle period of continuous probe performance per analysis procedure can also be extended for a particular metal by increasing the aspect ratio of the probe core 120 to orifice 111 diameter; that is, by increasing the inner diameter of the probe 120, so that core 120 takes a longer time to choke off.

One working prototype of the invention incorporates a die orifice 111 with a diameter of roughly 0.25 mm. This is more than an order of magnitude smaller than the smallest previously specified atomization die orifice. The ceramic construction of the atomization die 110 allows it to operate at the temperature of the molten bath with no cooling being necessary. Hence, no solid metal sleeve forms within the orifice 111. In practice, the atomization die 110 and probe body 100 can be constructed from either metallic or refractory materials, the specific choice being determined by the temperature and reactivity of the solution to be analyzed.

Figure 3:
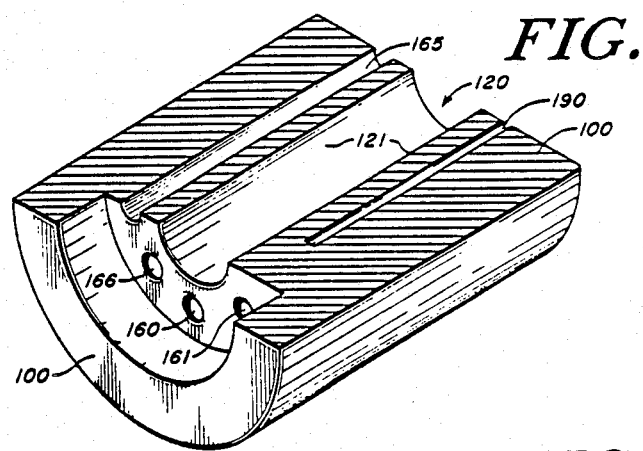
FIG. 3 is a detailed view of another preferred embodiment of the invention which illustrates the internal gas cooling channels, used to control the temperature of the interior wall of the probe.

FIG. 3 illustrates a further embodiment of the atomization probe 100. In this embodiment, the atomization probe is equipped with internal gas cooling channels 161 through 166. This gas cooling feature is not intended to protect the probe 100 from the high temperatures of the molten baths being sampled, as was the case with prior attempts to develop elemental sampling probes. As discussed above, it was this probe cooling requirement that resulted in the critical metal clogging problem within the probe core 120. Prior efforts (see U.S. Pat. No. 3,606,540) to develop elemental analysis probes based on gas atomization of liquid metal focused considerable attention on the minimization of metal powder contact with and subsequent buildup upon the interior probe wall. In spite of these efforts, probe failure due to metal clogging of the probe core occurred in a matter of a few minutes.

Given that the hot atomized metal powder tends to contact and stick to the interior wall of the probe 121, specific controlled gas cooling procedures have been developed to control this metal buildup. In the embodiment of FIG. 3, the gas cooling channels 161 through 166 serve to maintain the temperature of the interior wall of the probe 121 during the atomization process to below the melting temperature of the liquid metal 400 being analyzed. In some metal systems, the atomization gas alone may be adequate to cool the interior wall of the probe 121 sufficiently. In either case, the probe wall 121 is cooled sufficiently such that hot or liquid metal powder that strikes and sticks to it will freeze. If the probe wall 121 is above the melting temperature of the metal being analyzed, the metal powder that strikes and sticks to the probe wall will melt and flow back to the bottom of the probe, where it may interfere with the ongoing atomization process. The purpose of the gas cooling feature is to control the temperature of the interior probe wall 121 and thereby control the metal buildup and removal procedure. Upon completion of the atomization procedure, the gas flow through the cooling passages 161 through 166 is discontinued, which allows the temperature of the probe 100 to rise to that of the melt. Any metal buildup on the interior wall 121 of the probe then melts, flows to the bottom of the probe, and is removed by the procedure discussed earlier.

The temperature of the probe wall 121 can be monitored by an internal probe thermocouple 190. The cooling gas flows down channels of the type shown as 161 and 165, where it is diverted via appropriate slots in the top of the atomization die 110 to similar additional channels (not all shown) corresponding to channel 166, whence the gas flows up and out of the probe.

Figure 4:
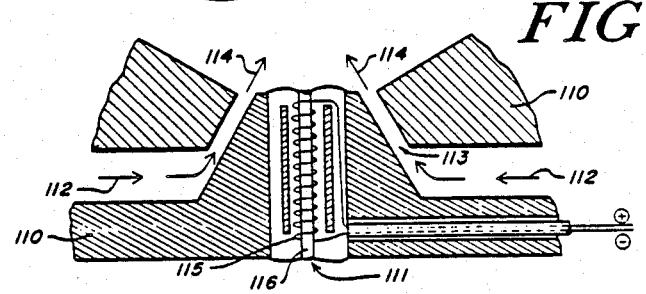
FIG. 4 is a detailed view of another preferred embodiment of the invention which illustrates the gas atomization die with an orifice heating element to eliminate freeze-off.

FIG. 4 illustrates a further emodiment of the atomization die 110. In this embodiment, the gas atomization die 110 is fitted with an orifice heating element 115 which eliminates the historical orifice freeze-off constraint. The heating element consists of a simple metal coil 115 which is wrapped around the central orifice sleeve 116. The particular metallic heating element selected is determined by the operating temperature requirements of the liquid system to be analyzed. For example, a tin melt can be maintained with a nichrome heater element, whereas for a ferrous system a tungsten or molybdenum filament may be suitable. The heat generated by the heating coil 115 serves to insulate the central orifice sleeve 116 from the cooling effect of the inert gas passing through the annular nozzle 113 of the die 110. The heating coil 115 may be connected to a heat control to provide only enough heat to ensure that the metal being atomized remains above its melting temperature as it passes through the orifice 111 or to control the rate or extent of metal build-up within the orifice 111.

The gas atomization probe 100 described in FIG. 1 is designed to provide rapid, in-process elemental analysis of molten metal and other liquid systems. Since the metal aerosol powder corresponds precisely to the elemental composition of the solution from which it was extracted, it can be analyzed to monitor the composition of any specific constituent element or the full range of elements present in the solution. The probe illustrated in FIG. 2 has been used to sample molten tin baths. The emission analysis of the probe sample was compared with that of a solid pin extracted from the same tin melt. The results of multiple probe and tin sample comparisons are indistinguishable within the scatter normally associated with atomic emission spectral analysis. This comparison included antimony, arsenic, bismuth, copper, lead, and iron in a tin matrix.

The probe is also designed for repetitive usage in the same bath or in sequential baths. Before each analysis procedure, the probe core 120 and metal aerosol conduit 125 must be purified of any residual material that might bias the analysis. This is accomplished before the probe 100 is placed in the melt 400, FIG. 1. Valve 130 is opened to the exhaust 131 position. A high pressure burst of inert gas 150 is released into the probe 100 via the probe gas inlet conduit 160 and atomization die 110. This gas exits the system through the open exhaust valve 131 and, to a lesser extent, the die orifice 111. The exhaust valve 131 is then switched to the closed position and the inert gas flow 150 is adjusted to provide a moderate positive pressure within the probe 120. This positive internal probe pressure allows the probe 100 to be submerged through the slag layer 500 and into the liquid metal 400 without having any slag or liquid metal enter the probe. In practice, the positive pressure within the probe 100 maintains a positive gas flow out through the orifice 111, which causes the probe 100 to bubble gently as it is submerged. Liquid metal is kept from entering the probe 100 by maintaining the internal gas pressure above that of the metallostatic head pressure. Consequently, the probe can be placed at any location or depth within the liquid bath. During this immersion process, any metal deposit left on the internal probe wall from a previous analysis melts and is ejected from the probe as discussed above. Alternatively, metal deposits may be removed by supplying heat to the probe from a source other than from the melt.

The liquid metal, gas atomization process is initiated by switching valve 130 to the open position, which connects the metal aerosol conduit directly to the gas pump 180, and simultaneously increasing the inert gas pressure and flow rate to the appropriate level necessary to sustain continuous liquid metal atomization. The liquid metal 400 is aspirated up through the die orifice 111 and, upon exiting the die, is atomized by the impinging gas jet 114. The metal powder is swept up by the inert gas flow and carried along the metal aerosol conduit 120 to the plasma flame 210 where the spectral emission is generated. This emission spectrum is analyzed by the emission spectrometer 200 and process control computer 300 to determine the elemental composition of the aerosol sample 140. This analysis can be completed in a matter of seconds. Preferably, the process control computer acts upon the results of the analysis and the thermocouple readout 190 to make the necessary process adjustments. While the analysis data may be available within seconds, it may be desirable in many cases to monitor the elemental composition of the bath continuously or intermittently for several minutes. When the measured elemental analysis matches that specified for the process, the probe analysis and the metallurgical process are discontinued. The gas atomization process is discontinued simply by closing valve 130 and simultaneously reducing the inert gas flow rate 150. The probe 100 is removed from the bath 400 and, as described above, is purged of any residual materials.

The probe 100 is designed to be reuseable; that is, it can provide several analyses before it must be replaced. In steelmaking operations, a single probe may provide consecutive analyses sufficient for a minimum of one eight-hour shift. The service life of the probe will, of course, depend upon the temperature and reactivity of the bath environment within which it is employed. Only the action end of the probe 100 need be replaced. The probe system is designed to facilitate quick and convenient replacement of the probe tip 100 via the probe/metal aerosol conduit interconnect 600. Standard gasline and electrical connections may be used at the interconnect 600, with the emphasis on ease of coupling to minimize the replacement effort required. It will be apparent that the invention permits use of the probe without removing it from the melt even to accomplish elimination of metal build-up in its interior, since valve 130 can be used to clear the system when the probe is immersed.

What is claimed is:

1. A method for performing continuous in-process generation of an aerosol powder for analysis thereof comprising the steps of:
   immersing in a melt a portion of an apparatus including an atomization die having an orifice suitable for aspiration along a flow axis, such orifice being in a size range at and immediately above the size which is just sufficient to permit both continuous generation of said powder by aspiration of the melt therethrough and in-process analysis of said powder, and having in at least one direction perpendicular to the flow axis a dimension less than approximately five millimeters;

aspirating the melt through the orifice so as to generate said powder by atomization;

conducting the powder to a remote location for analysis thereof via a gaseous transport medium;

raising the temperature of said portion of the apparatus in the melt so as to melt accumulated accretions therein;

ejecting the melted accretions from said portion of the apparatus so as to prepare the apparatus for a further period of powder generation.

2. A method according to claim 1, further including the step of supplying heat, other than from the melt, to the vicinity of the orifice.

3. A method according to claim 1, wherein the step of ejecting the melted accretions includes the step of causing the presence of a positive gas pressure within said portion of the apparatus so that there is at least some gas flow out from the apparatus.

4. A method for performing continuous in-process generation of an aerosol powder for analysis thereof, comprising the steps of:

immersing a portion of an apparatus including an atomization die having an orifice in a melt;

aspirating the melt through the orifice so as to generate said powder by atomization;

supplying heat, other than from the melt, to the vicinity of the orifice; and conducting the powder, through a portion of the apparatus subject to choking off by accumulation of accretions therein, to a remote location via a gaseous transport medium for analysis of said powder;

raising the temperature of said portion of the apparatus to melt off the accretions accumulated therein; and ejecting the melted accretions from said portion of the apparatus so as to prepare the apparatus for a further period of powder generation.

* * * * *